United States Patent [19]

Brennan et al.

[11] Patent Number: 5,391,650
[45] Date of Patent: Feb. 21, 1995

[54] BISBENZOCYCLOBUTENE THERMOSETTING COMPOUNDS AND PROCESS FOR PREPARING THE SAME

[75] Inventors: David J. Brennan; Jerry E. White; Daniel M. Scheck; Robert A. Kirchhoff, all of Midland, Mich.; Charles Z. Hotz, Walnut Creek, Calif.

[73] Assignee: The Dow Chemical Company, Midland, Mich.

[21] Appl. No.: 998,495

[22] Filed: Dec. 30, 1992

[51] Int. Cl.$^6$ .................. C08G 59/14; C08G 59/04
[52] U.S. Cl. ..................... 525/523; 526/280; 526/281; 528/97; 560/102; 564/82; 564/307; 568/38; 568/39; 568/47; 568/632; 568/633; 568/634
[58] Field of Search ............ 525/523; 568/632, 633, 568/634, 38, 39, 47; 560/102; 564/307, 82; 528/97; 526/280, 281

[56] References Cited

U.S. PATENT DOCUMENTS

| | | | |
|---|---|---|---|
| 4,540,763 | 9/1985 | Kirchhoff | 526/281 |
| 4,562,280 | 12/1985 | Gilpin et al. | 560/103 |
| 4,570,011 | 2/1986 | So | 560/8 |
| 4,638,001 | 1/1987 | Kuhla et al. | 514/212 |
| 4,639,442 | 1/1987 | Kuhla et al. | 514/212 |
| 4,642,329 | 2/1987 | Kirchhoff et al. | 526/284 |
| 4,661,193 | 4/1987 | Kirchhoff et al. | 156/307.3 |
| 4,711,964 | 12/1987 | Tan et al. | 548/461 |
| 4,724,260 | 2/1988 | Kirchhoff et al. | 546/112 |
| 4,743,399 | 5/1988 | Kirchhoff et al. | 252/512 |
| 4,743,600 | 5/1988 | Kuhla et al. | 514/212 |
| 4,783,514 | 11/1988 | Kirchhoff et al. | 526/281 |
| 4,788,187 | 11/1988 | Kuhla et al. | 514/212 |
| 4,795,827 | 1/1989 | Bruza et al. | 525/523 |
| 4,812,588 | 3/1989 | Schrock | 556/453 |
| 4,822,930 | 4/1989 | Liu | 570/206 |
| 4,826,997 | 5/1989 | Kirchhoff | 548/546 |
| 4,831,172 | 5/1989 | Hahn et al. | 556/419 |
| 4,891,455 | 1/1990 | Liu | 570/206 |
| 4,954,583 | 9/1990 | Wang | 525/507 |
| 4,954,584 | 9/1990 | Wang | 525/507 |
| 4,965,329 | 10/1990 | Kirchhoff | 526/259 |
| 5,068,396 | 11/1991 | Wang | 560/102 |
| 5,077,367 | 12/1991 | Campbell, Jr. et al. | 526/284 |
| 5,120,884 | 6/1992 | Thomas et al. | 568/734 |

OTHER PUBLICATIONS

Chem. Abstr., No. 26024, 117:26031v, vol. 117, 1992, p. 658, Thomas, P. J. et al.
Synth. Commun. 1991,21(22), 2335–40.
22–Physical Org. Chem., No. 20492, 85:20487x, vol. 85, 1976. Fleming, Ian et al.
Tetrahedron Lett. 1976, (11), 881–4.
Derwent, No. 02306, EP–43194, Jun. 19, 1980. Fisons Ltd.

*Primary Examiner*—Frederick Krass

[57] ABSTRACT

A compound having at least one 2-hydroxy-1,3-propylidene, 2-acetoxy-1,3-propylidene, or 2-alkoxy-1,3-propylidene moiety between two benzocyclobutene end moieties is prepared by (a) contacting a diepoxide species with a benzocyclobutene species containing a functionality capable of reacting with an epoxy group, (b) contacting an epoxy-containing benzocyclobutene species with a species containing two functionalities capable of reacting with an epoxy group, (c) contacting an epoxy-containing benzocyclobutene species with a benzocyclobutene species containing a functionality capable of reacting with an epoxy group, (d) contacting epichlorohydrin with benzocyclobutene species capable of reacting with an epoxy group, or (e) contacting epihalohydrin with benzocyclobutene species and difunctional species, wherein both species contain functionalities capable of reacting with epoxy groups. Each benzocyclobutene moiety is attached to the 2-hydroxy-1,3-propylidene moiety at the six-membered ring through oxygen or sulfur atoms, carboxyl, N-alkylimino, or 1,3-dioxyphenylene units. The unit linking the two benzocyclobutene moieties optionally contains aromatic moieties. The polymers prepared from the compounds are suitable for use in composites, coatings, adhesives, and binders. The polymers have outstanding processability and are mainly non-crystalline materials with low melt viscosities prior to the onset of curing.

33 Claims, No Drawings

BISBENZOCYCLOBUTENE THERMOSETTING COMPOUNDS AND PROCESS FOR PREPARING THE SAME

BACKGROUND OF THE INVENTION

This invention relates to thermosetting monomers and polymers having aromatic ether moieties and pendant hydroxyl moieties in the backbone chain, benzocyclobutene moieties at chain ends and to articles prepared therefrom.

Benzocyclobutene compositions are known to be useful in preparing thermoset and thermoplastic polymeric compositions. Such polymeric compositions are well-known as "self-curing" materials since they do not require an added curing agent, catalyst or comonomer to obtain effective crosslinking. Benzocyclobutenes cure upon application of heat. Such cured thermoset polymeric compositions have properties of rigidity, strength, and chemical resistance and are useful in many engineering applications such as coatings, structural laminates, adhesives, films, and composites. Desirable physical properties include enhanced chemical resistance, high tensile strength, high temperature resistance, electroinsulative or electroconductive properties, and oxidative stability.

A series of patents issued to Wang, illustrated by U.S. Pat. Nos. 4,954,583; 4,954,584; and 5,068,396, describes the preparation and curing of benzocyclobutene compositions that are prepared by contacting 1-benzocyclobutenecarboxylic acid with glycidyl ethers of bisphenols such as 2,2-bis(4-hydroxyphenyl)propane, wherein the linking group between the 1-benzocyclobutene carboxylate and the dioxydiphenyleneisopropylidene moiety is a 2-hydroxy-1,3-propylidene unit. The carboxy group connects the benzocyclobutene moiety to the remainder of the molecule by attachment to a carbon of the four-membered ring. Upon curing, such thermosetting resins have glass transition temperatures that are limited to 120° to 135° C.

It would be desirable to provide new thermosetting monomers having glass transition temperatures that are greater than 135° C. after curing.

SUMMARY OF THE INVENTION

In a first aspect, this invention is a compound having at least one 2-hydroxy-1,3-propylidene, 2-acetoxy-1,3-propylidene, or 2-alkoxy-1,3-propylidene moiety between two benzocyclobutene end moieties, wherein each benzocyclobutene moiety is attached to the 1,3-propylidene moiety at the six-membered ring through oxygen or sulfur atoms, carboxyl, N-alkylimino, or 1,3-dioxyphenylene units. The unit linking the two benzocyclobutene moieties optionally contains aromatic moieties.

In a second aspect, this invention is a process for preparing the above compound which comprises:

(a) contacting a diepoxide species with a benzocyclobutene species containing a functionality capable of reacting with an epoxy group, (b) contacting an epoxy-containing benzocyclobutene species with a species containing two functionalities capable of reacting with an epoxy group, (c) contacting an epoxy-containing benzocyclobutene species with a benzocyclobutene species containing a functionality capable of reacting with an epoxy group, (d) contacting an epihalohydrin with a benzocyclobutene species capable of reacting with an epoxy group, or (e) contacting an epihalohydrin with a benzocyclobutene species and a difunctional species, wherein both species contain functionalities capable of reacting with epoxy groups.

In a third aspect, this invention is a thermosetting polymer prepared from the above compound. The polymer of this invention is useful in preparing composites, coatings, adhesives, binders and films. The polymers have good flexural strength and modulus, and have glass transition temperatures between 86° and 220° C.

Surprisingly, the polymers are mainly non-crystalline, low viscosity materials which are self-curing and are easily processed.

DETAILED DESCRIPTION OF THE INVENTION

Definitions

The following terms are used in this application and have the meanings and preferred embodiments set out hereinafter unless otherwise specified.

Benzocyclobutene—Includes carbocyclic and heterocyclic arylcyclobutene (cyclobutarene) compounds, which consist of a cyclobutene ring fused to an aromatic moiety. It will be understood that "benzocyclobutene" is an art-recognized term. In the commonly-used non-systematic numbering system for benzocyclobutenes, the 1- and 2-positions are in the cyclobutene ring. The 3- and 6- positions are in an aromatic ring, adjacent to the cyclobutene ring. The 4- and 5-positions are meta- to the cyclobutene ring. The simplest member of the series, benzocyclobutene, is formally identified as bicyclo[4.2.0]octa-1,3,5-triene. A compound, formally identified as 3-bromobicyclo[4.2.0]octa-1,3,5-triene, is commonly known as 4-bromobenzocyclobutene. The common names will be used in the specification and claims. Methods of making cyclobutarene precursors are disclosed in U.S. Pat, Nos. 4,562,280 and 4,570,011; herein incorporated by reference. Suitable cyclobutarene moieties and their preparation are disclosed in U.S. Pat. Nos. 4,540,763; 4,724,260; 4,831,172; 4,783,514; 4,642,329; 4,743,399; 4,661,193; and 4,812,588, all herein incorporated by reference. Preferably, the cyclobutarene moiety is a benzocyclobutene moiety.

Arylcyclobutene—Refers to an aryl group which contains one or more cyclobutene rings fused to at least one of the aromatic rings.

Polyarylcyclobutene—Refers to a compound containing 2 or more arylcyclobutene moieties connected either by a direct bond or bridging member. Bridging members comprise (1) a polyvalent inorganic moiety or (2) a polyvalent organic moiety containing (a) one or more heteroatoms such as O, P, N, Si or S or (b) one or more aromatic radicals. The bridging member or direct bond connects the arylcyclobutene moieties through the aryl radical.

Aromatic moiety—Refers to carbocyclic or heterocyclic ring compound containing $(4n+2)n$ electrons in an orbital ring as described in Morrison & Boyd, Organic Chemistry, 3rd ed., 1973. This property is also known as resonance stabilization or delocalization.

The aromatic moiety can be further substituted with a variety of monovalent moieties. Examples of suitable monovalent moieties include $—NO_2$, $—CN$, Br, I, Cl, F, H, $—OH$, $—PR_2$, $—CO_2R$, $—CHO$,

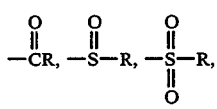

hydrocarbyl, hydrocarbyloxy, hydrocarbylthio, —OR, —NHR, and —NR₂, wherein R is H or alkyl.

Hydrocarbyl—Refers to any organic moiety containing only carbon and hydrogen atoms. The term hydrocarbyl means a monovalent hydrocarbon moiety including the following: alkyl, alkenyl, alkynyl, cycloalkyl, cycloalkenyl, cycloalkynyl, aryl, aliphatic and cycloaliphatic aralkyl and alkaryl, and the like.

Hydrocarbylene—Refers to a divalent hydrocarbon moiety including the following: alkylene, alkenylene, alkynylene, cycloalkylene, cycloalkenylene, cycloalkynylene, arylene, aliphatic and cycloaliphatic aralkylene and alkarylene, and the like.

Aliphatic—Refers to straight- and branched-, and saturated and unsaturated, hydrocarbon chains, that is alkyl, alkenyl or alkynyl.

Cyclo-aliphatic—Refers to saturated and unsaturated cyclic hydrocarbons, that is, cycloalkenyl, cycloalkynyl, and cycloalkyl.

Aryl—Refers to any aromatic moiety such as biphenyl, phenyl, naphthyl, phenanthrenyl, anthracenyl and two aryl groups bridged by an alkylene group or heteroatoms such as oxygen and sulfur.

Aralkyl—Refers to an alkyl, alkenyl or alkynyl group substituted with an aryl group.

Alkaryl—An alkyl-, alkenyl- or alkynyl-substituted aryl substituent.

Cycloalkyl—Alkyl groups containing one or more cycloaliphatic rings.

Cycloalkenyl—Mono- and polycyclic groups containing one or more double bonds.

Acyl—Monovalent moiety containing a carbonyl group through which attachments occur.

Divalent organic moiety—Any organic moiety bonded to two other moieties. The divalent organic moiety may also contain one or more heteroatoms, such as oxygen, nitrogen, phosphorus, silicon, or sulfur. Preferred divalent organic moieties include aliphatics such as alkylene, alkenylene, and alkynylene; arylenes such as the following;

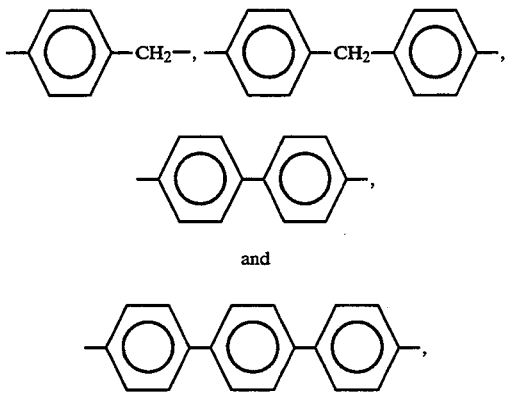

sulfones, and carbonyl-containing species. More preferred organic moieties include arylenes, and carbonyl-containing species.

Divalent inorganic moiety—Any inorganic moiety which can bond to two other moieties. Preferred inorganic moieties include oxygen and sulfur. The most preferred inorganic moiety is oxygen.

Carbocyclic—The aromatic moiety has only carbon atoms in its nucleus. Preferred carbocyclic aromatic moieties include benzene, naphthalene, phenanthrene, anthracene, a biaryl moiety or two or more aromatic radicals, bridged by alkylene or cycloalkylene moieties. More preferred carbocyclic aromatic radicals include benzene, naphthalene, biphenyl, binaphthyl, diphenylalkane or diphenylcycloalkane radicals. The most preferred carbocyclic aromatic radical is a benzene radical, which, when fused to a cyclobutene ring, produces the simplest member of the series, benzocyclobutene.

Thermosetting monomers or compounds—Materials that contain more than one active site which leads to the formation of thermoset resins that are typically highly crosslinked. In many thermoset resins, the use of catalysts, curing agents or comonomers is necessary in order to accomplish effective reaction or curing of the crosslinkable functionalities. For example, epoxy resins require the use of catalytic or stoichiometric amounts of curing agents to cause the curing or crosslinking to take place at an acceptable rate.

Thermosetting resins—Compositions which solidify irreversibly upon curing.

DESCRIPTION OF THE INVENTION

Preferably, the compound of this invention is represented by the formula:

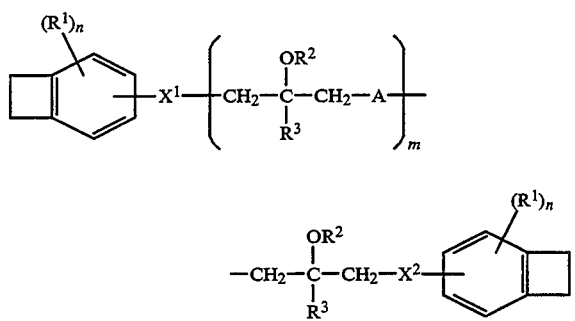

wherein $R^1$ is a halogen, a monovalent hydrocarbyl or substituted hydrocarbyl moiety; each $R^2$ is independently hydrogen, monovalent hydrocarbyl, substituted hydrocarbyl or acyl moieties; each $R^3$ is independently hydrogen, monovalent hydrocarbyl or substituted hydrocarbyl moieties, wherein the substituent(s) is a monovalent moiety which is inert in the reactions used in preparing the compound; $X^1$ is a divalent organic or inorganic moiety; $X^2$ is a divalent organic or inorganic moiety that may be the same as or different than $X^1$; each A is individually a divalent moiety. Preferably, each A is represented by one of the formulae:

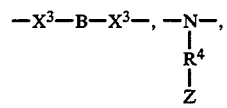

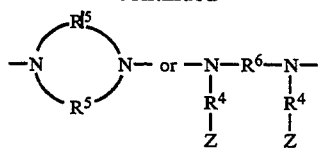

wherein B is individually a divalent organic moiety; $R^4$ is $C_2$–$C_{10}$ hydrocarbylene or substituted $C_2$–$C_{10}$ hydrocarbylene, $R^5$ is $C_2$–$C_{10}$ alkylene or substituted $C_2$–$C_{10}$ alkylene; $R^6$ is $C_2$–$C_{20}$ hydrocarbylene or substituted $C_2$–$C_{20}$ hydrocarbylene, wherein the substituent(s) is a monovalent moiety which is inert in the reactions used in preparing the compound; Z is hydrogen or a monovalent organic or inorganic moiety; $X^3$ is a divalent organic or inorganic moiety that may be the same as or different than $X^1$ and $X^2$; n=0–3; and m=0–1000. Examples of such substituents include cyano, halo, amido, hydroxy and hydroxyalkyl.

More preferably, $R^1$ is halogen, alkyl, or aryl; $R^2$ is individually hydrogen, alkyl, cycloalkyl, aralkyl, aryl, or acyl; $R^3$ is individually hydrogen, alkyl, cycloalkyl, aralkyl, or aryl; $X^1$ is a divalent organic or inorganic moiety such as oxygen, sulfur, N-substituted imino, N-substituted sulfonamido, carboxyl, or dioxyarylene; $X^2$ is independently a divalent organic or inorganic moiety such as oxygen, sulfur, N-substituted imino, N-substituted sulfonamido, carboxyl, or dioxyarylene; B is predominantly arylene or substituted arylene, alkylene or substituted alkylene, araalkylene or substituted araalkylene; $R^4$ is $C_2$–$C_{10}$ alkylene or phenylene, substituted $C_2$–$C_{10}$ alkylene or phenylene, wherein the substituent is alkylamido, hydroxyl, alkoxy, alkylcarbonyl, aryloxy, halo, or cyano; $R^5$ is $C_2$–$C_{10}$ alkylene or substituted $C_2$–$C_{10}$ alkylene, wherein the substituent is hydrogen, alkylamido, hydroxyl, alkoxy, alkylcarbonyl, aryloxy, halo, or cyano; $R^6$ is $C_2$–$C_{20}$ alkylene or substituted $C_2$–$C_{20}$ alkylene, wherein the substituent is hydrogen, alkylamido, hydroxyl, alkoxy, alkylcarbonyl, aryloxy, halo, or cyano; Z is hydrogen, alkylamido, hydroxyl, alkoxy, alkylcarbonyl, aryloxy, halo, or cyano; $X^3$ is independently a divalent organic or inorganic moiety such as oxygen, sulfur, N-substituted imino, N-substituted sulfonamido, carboxyl; n=0 or 1; m=0–50.

Most preferably, n=0; m=0–5; $R^2$ is individually hydrogen, alkyl, or acyl; $R^3$ is hydrogen; $X^1$ is oxygen, sulfur, N-substituted imino, N-substituted sulfonamido, carboxyl, or dioxyarylene; $X^2$ is independently oxygen, sulfur, N-substituted imino, N-substituted sulfonamido, carboxyl, or dioxyarylene; B is isopropylidenediphenylene, fluorenylidenediphenylene, dinitrofluorenylidenediphenylene, phenylene, sulfonyldiphenylene, biphenylene, biphenylene oxide, biphenylene sulfide, methylenediphenylene, phenylethylidenediphenylene, tetrabromoisopropylidenediphenylene, naphthylene, or bis[(N-phenyleneamido)propylidene, bis(benzamido)ethylene, amidodiphenylene, or [bis(N-methylenephthalimido)]carbonyl; $R^4$ is ethylene, propylene, or phenylene, $R^5$ is ethylene or propylene; $R^6$ is ethylene, propylene, or phenylene; Z is hydrogen or hydroxyl; $X^3$ is oxygen, sulfur, N-substituted imino, N-substituted sulfonamido, or carboxyl. Other preferred ranges for "m" include 0–10 and 1–25.

The compounds of this invention are preferably prepared by contacting:

(a) a diepoxide species with a benzocyclobutene species containing a functionality capable of reacting with an epoxy group, (b) an epoxy-containing benzocyclobutene species with a species containing two functionalities capable of reacting with epoxy groups, (c) an epoxy-containing benzocyclobutene species with a benzocyclobutene species containing a functionality capable of reacting with an epoxy group, (d) an epihalohydrin with a benzocyclobutene species capable of reacting with an epoxy group, or (e) an epihalohydrin with a benzocyclobutene species and difunctional species, wherein both species contain functionalities capable of reacting with epoxy groups;

under conditions sufficient to cause the epoxy species to react with the functionalities capable of reacting with an epoxy group, wherein pendant hydroxyl moieties are formed during the linking of the benzocyclobutenyl moiety to the remainder of the molecule.

The temperature for performing the process of this invention is from about 50° C. to a temperature at which dimerization or oligomerization of the benzocyclobutene reactant or product becomes a significant side reaction. The upper temperature limit can be determined empirically by known methods, such as by following the progress of the reaction using gas chromatography. It has been found that appreciable dimerization or oligomerization occurs at temperatures above 200° C., or even above 180° C. Therefore, it is preferred to carry out the process of this invention at temperatures below 200° C., more preferably below 180° C., and most preferably at or below 150° C. Preferably, the compounds are prepared in the melt, i.e. in the absence of solvent, but can optionally employ the use of organic solvents in order to ensure homogeneous reaction mixtures at such temperatures. Preferred organic solvents include diethylene glycol dimethyl ether, methoxyisopropanol, and ethanol. Most preferred conditions for preparing such thermosetting compounds are set forth in the following working examples, and include the use of catalysts such as onium salts, strong bases, or uncatalyzed reactions between epoxide species and primary or secondary amines. By "onium" is meant a salt in which the cation is an onium cation such as quaternary ammonium or phosphonium or ternary sulfonium. By a strong base is meant hydroxide, with sodium hydroxide being especially preferred.

Suitable onium catalysts include quaternary ammonium or quaternary phosphonium salts. Preferred onium catalysts are tetrakis(n-butyl) ammonium bromide and the corresponding chloride, iodide, and fluoride. Most preferred onium catalysts are alkyltriarylphosphonium halides or acetates, such as ethyltriphenylphosphonium iodide, ethyltriphenylphosphonium bromide and ethyltriphenylphosphonium acetate and tetraarylphosphonium halides, such as tetraphenylphosphonium bromide.

Suitable functionalities capable of reacting with epoxy groups include, but are not limited to: —OH, —$NH_2$, —NHR, —$CO_2H$, —SH, and —CONHR, wherein R is hydrogen or $C_1$ to $C_{20}$ hydrocarbyl radical. Preferred functionalities are —OH (phenolic), —$NH_2$, —NHR, —$CO_2H$, —SH, and —CONHR. Most preferred functionalities are —OH (phenolic), —NHR, and —$CO_2H$.

Suitable benzocyclobutene species capable of reacting with an epoxy group include, but are not limited to, the hydroxyl-substituted benzocyclobutenes, the amino-substituted benzocyclobutenes, the mercapto-substituted benzocyclobutenes and benzocyclobutene-4-carboxylic acid.

Examples of hydroxyl-substituted benzocyclobutene compounds include 3-hydroxybenzocyclobutene and 4-hydroxybenzocyclobutene.

Other suitable hydroxyl-substituted benzocyclobutene compounds include, but are not limited to, compounds of the formula:

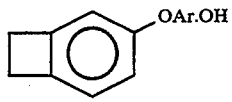

wherein Ar is an aryl hydrocarbyl moiety, preferably a benzene or naphthalene ring. The aryl group can optionally be substituted with up to three substituents other than hydrogen. These substituents can be independently alkyl, aryl, halogen or cyano groups.

Other suitable hydroxyl-substituted benzocyclobutene compounds include those of the formula:

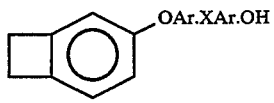

wherein Ar is a benzene ring and X is a divalent linking group or a direct chemical bond. The divalent linking group can be oxygen, sulfur, or a $C_1$–$C_4$ saturated alkylene group optionally substituted with fluorine atoms. The aryl groups can optionally be substituted with up to three substituents other than hydrogen. These substituents can be independently alkyl, aryl, halogen or cyano groups.

Several of the hydroxyl-substituted benzocyclobutene compounds are prepared by reacting a suitably functionalized benzocyclobutene compound with a dihydroxyaromatic compound in the presence of a base, a copper catalyst, and an organic solvent. The reaction is known in the art as the Ullmann ether synthesis. The benzocyclobutene compound is functionalized with a leaving group, preferably chloro, bromo, or iodo, most preferably bromo. The dihydroxyaromatic compounds are of the form HO—Ar—OH or HO—Ar—X—Ar—OH, optionally substituted with alkyl, aryl, halogen or cyano groups described above.

Examples of suitable dihydroxyaromatic compounds include, but are not limited to, resorcinol, 1,3-dihydroxynaphthalene, 1,6-dihydroxynaphthalene, 2,7-dihydroxynaphthalene, 4,4'-dihydroxybiphenyl, bis(4-hydroxyphenyl)methane, 2,2-bis(4-hydroxyphenyl)propane, 2,2-bis(3-hydroxyphenyl)propane, and 2,2-bis(4-hydroxyphenyl)hexafluoropropane. The most preferred dihydroxyaromatic compound is resorcinol. The dihydroxyaromatic compound is employed in a molar excess relative to the benzocyclobutene compound to ensure predominantly monosubstitution. An excess of from 3 to 10 moles, preferably from 4 to 5 moles, of dihydroxyaromatic compound per mole of benzocyclobutene is employed. Suitable bases include, but are not limited to, alkali metal hydroxides, alkali metal alkoxides, alkali metal carbonates, alkali metal alkyl compounds and alkali metal hydrides. Examples of preferred bases include potassium carbonate, sodium carbonate, potassium hydroxide, sodium hydroxide, sodium methoxide, sodium ethoxide, potassium tert-butoxide and sodium hydride. The most preferred bases are potassium carbonate and sodium methoxide. Suitable solvents include, but are not limited to, dimethylacetamide, dimethylformamide, diglyme and pyridine. The most preferred solvents are pyridine and dimethylacetamide. Suitable catalysts include copper (I) and copper (II) salts. Examples of suitable catalysts include the halide, oxide and acetate salts of copper (I) and copper (II). The most preferred catalysts are copper (I) chloride and copper (I) bromide. The catalyst is employed at a level of 0.01 to 0.20 moles per mole of benzocyclobutene compound, preferably from 0.05 to 0.10 moles per mole of benzocyclobutene compound. A catalyst promoter can also optionally be employed. The preferred catalyst promoter is 1,10-phenanthroline.

Examples of amino-substituted benzocyclobutenes include, but are not limited to, 4-(N-methylamino)benzocyclobutene, 4-(N-ethylamino)benzocyclobutene, 4-(N-propylamino)benzocyclobutene, and 4-(N-butylamino)benzocyclobutene. A process for preparing these compounds is described in copending application U.S. Ser. No. 763,016, filed on Sep. 20, 1992 now U.S. Pat. No. 5,274,135, incorporated herein by reference.

An example of mercapto-substituted benzocyclobutenes is 4-mercaptobenzocyclobutene. A process for preparing these compounds is described in U.S. Pat. No. 4,540,763, incorporated herein by reference.

Suitable epoxy-containing benzocyclobutene species include 4-glycidyloxybenzocyclobutene, 4-(N-glycidyl-N-methylamino)benzocyclobutene, 4-(3-glycidyloxyphenoxy)benzocyclobutene, and glycidyl benzocyclobutene-4-carboxylate, with 4-glycidyloxybenzocyclobutene being preferred.

Suitable difunctional species capable of reacting with an epoxide group include bisphenols, dicarboxylic acids, bis-secondary amines, primary amines, dithiols, bis-(N-alkylsulfonamides), and compounds that contain two different functionalities capable of reacting with epoxide groups.

Suitable bisphenols are listed in U.S. Pat. Nos. 5,115,075, 5,089,588, 4,480,082 and 4,438,254, which are incorporated herein by reference. Preferred bisphenols include the amide-containing bisphenols such as N,N'-bis(hydroxyphenyl)alkylenedicarboxamides, N,N'-bis(hydroxyphenyl)arylenedicarboxamides, bis(hydroxybenzamido)alkanes or bis(hydroxybenzamido)arenes, N-(hydroxyphenyl)-hydroxybenzamides, 2,2-bis(hydroxyphenyl)acetamides, isopropylidenebisphenol, bis(4-hydroxyphenyl)fluorene, hydroquinone, resorcinol, 4,4' sulfonyldiphenol, thiodiphenol, 4,4'dihydroxybenzophenone, tetrabromoisopropylidenebisphenol, dinitrofluorenylidenediphenylene, 4,4'-biphenol, 4,4'-dihydroxybiphenylene oxide, bis(4-hydroxyphenyl)methane, α,α-bis(4-hydroxyphenyl)ethylbenzene, 2,6-dihydroxynaphthylene, N,N'-bis(3-hydroxyphenyl)-glutaramide, N,N'-bis(3-hydroxyphenyl)adipamide, 1,2-bis(4-hydroxybenzamido)ethane, 1,3-bis(4-hydroxybenzamido)benzene, N-(4-hydroxyphenyl)-4-hydroxybenzamide, and 2,2-bis(4-hydroxyphenyl)acetamide. Other preferred bisphenols are the imide-containing bisphenols listed in copending U.S. application Ser. No. 884,673, filed on May 18, 1992 now U.S. Pat. No. 5,246,751, which is incorporated herein by reference. Most preferred bisphenols are isopropylidenebisphenol, 9,9-bis(4-hydroxyphenyl)fluorene, hydroquinone, and 4,4'-sulfonyldiphenol.

A process for preparing the amide-containing bisphenols is described in U.S. Pat. No. 5,134,218, incorporated herein by reference.

Suitable dicarboxylic acids include, but are not limited to, phenylene dicarboxylic acids, biphenylene dicarboxylic acids, naphthalene dicarboxylic acids, and alkylene dicarboxylic acids. Preferred dicarboxylic acids include isophthalic acid, terephthalic acid, 4,4'-biphenylene dicarboxylic acid, 3,4'-biphenylene dicarboxylic acid, 3,3'-biphenylene dicarboxylic acid, 2,6-naphthalenedicarboxylic acid, and adipic acid. Most preferred dicarboxylic acids are isophthalic acid, terephthalic acid, 4,4'-biphenylene dicarboxylic acid, and 2,6-naphthalenedicarboxylic acid.

Suitable bis-secondary amines include, but are not limited to, piperazine and substituted piperazines, e.g. dimethylpiperazine and 2-methylamidopiperazine; bis(N-methylamino)benzene, 1,2-bis(N-methylamino)ethane, and N,N'-bis(2-hydroxyethyl)ethylenediamine. Preferred bis-secondary amines are piperazine, dimethylpiperazine, and 1,2-bis(N-methylamino)ethane. The most preferred bis-secondary amine is piperazine.

Suitable primary amines include, but are not limited to, aniline and substituted anilines, e.g. 4-(methylamido)aniline, 4-methylaniline, 4-methoxyaniline, 4-tert-butylaniline, 3,4-dimethoxyaniline, 3,4-dimethyaniline; alkylamines, and substituted alkyl amines, e.g. butylamine and benzylamine; and alkanol amines; e.g. 2-aminoethanol and 1-aminopropan-2-ol. Preferred primary amines are aniline, 4-methoxyaniline, 4-tert-butylaniline, butylamine, and 2-aminoethanol. Most preferred primary amines are 4-methoxyaniline and 2-aminoethanol.

Suitable dithiols include those represented by the formula HS—$R^7$—SH, wherein $R^7$ is a predominantly hydrocarbylene moiety or a divalent aromatic moiety. Preferably, $R^7$ is (1) an alkylene moiety having from 2 to about 20 carbons or a heteroalkylene containing an alkylene group(s) and a heteroatomic moiety(s) which is oxygen, sulfur, sulfonyl or sulfoxyl or (2) an arylene having from 5 to 25 carbons or heteroarylene containing an arylene ring wherein the ring is interrupted with said heteroatomic moiety, provided that the arylene group is optionally substituted with alkyl, alkoxy, halo, nitro or cyano. The most preferred dithiol is 4,4'-dimercaptodiphenyl ether (DMPE).

Suitable disulfonamides include, but are not limited to, N,N'-dimethyl-1,2-benzenedisulfonamide, N,N'-dimethyl-1,3-benzenedisulfonamide, N,N'-dimethyl-1,4-benzenedisulfonamide, N,N'-bis(2-hydroxyethyl)-1,2-benzenedisulfonamide, N,N'-bis(2-hydroxyethyl)-1,3-benzene-disulfonamide, -N,N'-bis(2-hydroxyethyl)-1,4-benzenedisulfonamide, N,N'-diphenyl-1,2-benzenedisulfonamide, N,N'-diphenyl-1,3-benzenedisulfonamide, N,N'-1,4-benzenedisulfonamide, N,N'-dimethyl-4,4'-biphenylenedisulfonamide, N,N'-dimethyl-4,4'-oxydiphenylenedisulfonamide, N,N'-dimethyl-4,4'-thiodiphenylenedisulfonamide, N,N'-dimethyl-4,4'-methylenediphenylenedisulfonamide, and N,N'-dimethyl-4,4-sulfonayldiphenylenedisulfonamide. Preferred disulfonamides include N,N'-dimethyl-1,3-benzenedisulfonamide and N,N'-bis(2-hydroxyethyl)- 4,4-biphenyldisulfonamide. The disulfonamides are prepared by reactions of primary aliphatic or aromatic amines with bis(chlorosulfonyl) alkanes and arenes. These sulfonamides are described in U.S. Pat. No. 5,149,768, incorporated herein by reference.

Suitable compounds that contain two different functionalities capable of reacting with epoxide groups include hydroxybenzoic acids, N-alkylamino acids, N-alkylaminophenols, and N-alkylsulfonamidophenols. Preferred are salicylic acid and 4-hydroxybenzoic acid. Most preferred is 4-hydroxybenzoic acid.

Suitable diepoxides include the diglycidyl ethers of the dihydridic phenols mentioned previously, α,ω-diglycidyloxyisopropylidene-bisphenol-based phenoxy resins (commercially known as D.E.R. TM 300 and 600 series epoxy resins), α,ω-diglycidyloxy tetrabromo isopropylidene-bisphenol-based phenoxy resins, such as Quatrex TM 6410, a product of The Dow Chemical Company, diglycidylamines of the bis-secondary and primary amines mentioned previously, and diglycidyl esters of the dicarboxylic acids mentioned previously. Other suitable diepoxides are described in U.S. Pat. No. 5,089,588 and in copending application U.S. Ser. No. 800,340, filed on Nov. 26, 1991 now abandoned, which are incorporated herein by reference. More preferred diepoxides are the diglycidyl ethers of isopropylidenebisphenol, 9,9-bis(4-hydroxyphenyl)fluorene, hydroquinone, 2,6-dihydroxynapthylene, 4,4'-biphenol, 4,4'-sulfonyldiphenol, thiodiphenol, 4,4'-dihydroxybenzophenone, and bis(4-hydroxyphenyl)methane; and the D. E. R. TM 300 and 600 series epoxy resins. Most preferred diepoxides are the diglycidyl ethers of isopropylidenebisphenol, 9,9-bis(4-hydroxyphenyl)fluorene, and hydroquinone.

Suitable epihalohydrins include epichlorohydrin, epibromohydrin, epiiodohydrin, methylepichlorohydrin, methylepibromohydrin, methylepiiodohydrin, ethylepichlorohydrin, ethylepibromohydrin, ethylepiiodohydrin, and mixtures thereof, and the like. Most preferred is epichlorohydrin.

The present invention is illustrated in further detail by the following examples. The examples are for the purposes of illustration only, and are not to be construed as limiting the scope of the present invention. All parts and percentages are by weight unless otherwise specifically noted.

Illustrative Embodiments

The following compounds are used in the examples:

4-hydroxybenzocyclobutene (BCB-phenol)

A representative synthesis is reported by L. Horner, et al., Chem. Ber., volume 93 (1960), page 1774, incorporated herein by reference. Other processes for preparing 4-hydroxybenzocyclobutene are described in copending application U.S. Ser. No. 922,651, filed on Jul. 30, 1992 now U.S. Pat. No. 5,227,536, and in U.S. Pat. No. 5,120,884, both incorporated herein by reference.

Benzocyclobutene-4-carboxylic acid

A process for preparing this compound is described in U.S. Pat. No. 4,540,763, incorporated herein by reference.

4-glycidyloxybenzocyclobutene

A process for preparing this compound is described in the following Example 1.

9,9-bis(4-diglycidyloxyphenyl)fluorene

A process for preparing this compound is described in U.S. Pat. No. 4,882,370 and in copending U.S. application Ser. No. 800,340, filed on Nov. 26, 1991, now abandoned both incorporated herein by reference.

N-(4-hydroxyphenyl)-4-hydroxybenzamide

A process for preparing this compound is described in U.S. Pat. No. 5,134,218, incorporated herein by reference.

4-bromobenzocyclobutene

This compound can be prepared in accordance with the process described in U.S. Pat. No. 4,822,930 or U.S. Pat. No. 4,540,763, both incorporated herein by reference.

D.E.R. ™ 661, 662 and 669—These are diglycidyloxyisopropylidene-bisphenol-based phenoxy resins manufactured by The Dow Chemical Company, Midland, Mich. D.E.R. ™ 661 has an epoxy equivalent weight of 475–575 and a Durran's melting point of 70°–78° C.; D.E.R. ™ 662 has an epoxy equivalent weight of 575– 700 and a Durran's melting point of 80°–90° C.; and D.E.R. ™ 669 has an epoxy equivalent weight of 3500–5500 and a Durran's melting point of 135°–155° C.

4-mercaptobenzocyclobutene

This compound can be prepared in accordance with the process described in U.S. Pat. No. 4,540,763, incorporated herein by reference.

4-(N-methylamino)benzocyclobutene

This compound can be prepared in accordance with the process described in copending application U.S. Ser. No. 763,016, filed on Sep. 20, 1992, now U.S. Pat. No. 5,274,135 incorporated herein by reference.

4-(3-hydroxyphenoxy)benzocyclobutene

The preparation of this compound is described in the following Example 2.

EXAMPLE 1

A. Preparation of 4-glycidyloxybenzocyclobutene

To a 2L three-neck round-bottom flask fitted with an overhead mechanical stirrer assembly, a water-cooled condenser with nitrogen inlet adapter, and thermometer attached to a temperature control unit, is added 4-hydroxybenzocyclobutene (213 g, 1.77 mol), epichlorohydrin (700 mL, 828 g, 8.95 mol), and benzyltrimethylammonium chloride (PhCH$_2$NMe$_3$Cl) (0.2 g, 1.1 mmol). The solution is heated at 90° C. for 72 hours under an atmosphere of nitrogen. The solution is then cooled to 25° C. and maintained at 25°–35° C. as 50% aqueous sodium hydroxide (150 mL, 216 g, 108 g NaOH, 2.7 mol NaOH) is added dropwise over a 30-minute period. On completion of addition, the reaction mixture is stirred for an additional two hours at 25° C. then poured into one liter of methylene chloride. The mixture is washed with two 500 mL portions of water. The organic layer is separated from the aqueous layer, dried over magnesium sulfate, and filtered, and the solvent is removed under reduced pressure yielding an oil. The oil is distilled under reduced pressure to yield a clear, water-white liquid and the fraction distilling at 100°–110° C. (0.5 mmHg) (ca. 150 mL) is collected. The liquid crystallizes on standing to form a white solid. Yield is 151 g (48%). The material is identified as 4-glycidyloxybenzocyclobutene by $^1$H and $^{13}$C NMR spectroscopy.

B. Preparation of Compound 1

To a 250 mL one-neck round-bottom flask is added 4-hydroxybenzocyclobutene (41.33 g, 0.344 mol), 4-glycidyloxybenzocyclobutene (60.70 g, 0.344 mol), and ethyltriphenylphosphonium iodide (EtPh$_3$PI) (0.50 g, 1.2 mmol, 0.5 weight percent). The flask is fitted with a Teflon ® (trademark of E. I. du Pont de Nemours & Co. Inc.) coated magnetic stir bar, a septum, thermocouple, and a syringe needle connected to a nitrogen line. The mixture is heated under nitrogen and gives a homogeneous melt at 100° C. Near 130° C., an exotherm develops which causes the melt to reach a temperature of 160° C. The melt is cooled to 130° C. with use of a water bath and maintained at 130° C. for 24 hours. The slightly viscous melt is poured into a jar to yield 100.8 g (99%) of a light yellow fluid which crystallizes on standing. Differential scanning calorimetry (DSC) detects a melting endotherm with a peak maximum at 80° C. The compound has a melt viscosity of 27 centipoise (cps) at 85° C. $^1$H and $^{13}$C NMR spectroscopy are used to confirm the structure of compound 1.

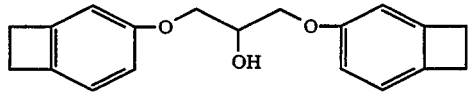

C. Monomer Curing by Differential Scanning Calorimetry

A 20 mg sample of Compound 1 is analyzed by differential scanning calorimetry (DSC) under nitrogen using the following schedule: 50°–300° C. at 10° C./minute. Compound 1 exhibits an exotherm between 200° and 300° C. with T$_{max}$ of 260° C. (curing of the BCB groups). Subsequent DSC scans shows a glass transition temperature (Tg) of 215° C. for the cured resin (Table 1).

D. Bulk Monomer Curing

Compound 1 (ca. 100 g) is melted and degassed under vacuum at 120° C. for one hour in preparation for molding. An upright mold consisting of a Teflon ® gasket between two steel plates is preheated to 180° C. and the molten resin is poured in. The mold is then placed into an oven and cured under an atmosphere of nitrogen according to the following cure schedule: 190° C., two hours; 200° C., two hours; 220° C., two hours; and 260° C., two hours The oven is turned off and allowed to cool to room temperature before the mold is removed. The resulting polymer plaque is void-free and has a density of 1.22 g/cc. Properties of the cured resin are measured and are reported in Table 2.

E. Additional Compounds

For the purposes of further exemplification, Compounds 2–4 are prepared by reacting 4-glycidyloxybenzocyclobutene (1.76 g, 10.0 mmol) with 4-mercaptobenzocyclobutene (1.36 g, 10.0 mmol), benzocyclobutene-4-carboxylic acid (1.48 g, 10.0 mmol), and 4-(N-methylamino)benzocyclobutene (1.33 g, 10.0 mmol), respectively, in a 20 mL flask fitted with a magnetic stir bar, thermocouple, and nitrogen inlet. EtPh$_3$PI (0.02 g) is added to the flask during the preparation of Compounds 2 and 3, but is not required during the preparation of Compound 4. The reactants are heated at 130° C.

with stirring under nitrogen for 3 hours. Compounds 2–4 are identified by 1H and 13C NMR spectroscopy and are cured according to the method described in Example 1, Part C. Glass transition temperatures of the cured resins are given in Table 1.

EXAMPLE 2

A. Preparation of 4-(3-hydroxyphenoxy)benzocyclobutene

Resorcinol (176.2 g, 1.60 moles), dimethylacetamide (DMAC) (550 mL), toluene (75 mL), potassium carbonate (55.2 g, 0.40 moles), 4-bromobenzocyclobutene (73.2 g, 0.40 moles), and cuprous chloride (3.96 g, 0.040 moles) are placed in a 1000 mL 3-necked flask. The flask is equipped with a water separating trap, reflux condenser, nitrogen inlet, and thermometer. The system is purged with nitrogen. The mixture is then heated to reflux, and water and toluene are collected in the trap. Toluene (about 25 mL) is distilled out of the reaction mixture and removed from the trap, until the temperature in the flask reaches 153° C. A sample, removed from the reaction after 5 hours of reflux and analyzed by gas chromatography (GC), shows little bromobenzocyclobutene remaining. The reaction is allowed to cool to room temperature after 6 hours of reflux. During the reaction, the temperature in the flask rises slightly to 156° C. by the end of the reaction.

The reaction mixture is transferred to a 1000 mL single-neck flask, and most of the solvent is removed on a rotary evaporator. The remaining concentrated solution is poured into a separatory funnel along with water (600 mL) and toluene (600 mL). The layers are separated and the aqueous layer is extracted with toluene (200 mL). The combined organic layers are washed with two 400 mL portions of water. The toluene is then removed on a rotary evaporator and the residue, a brown liquid, is distilled on a kugelrohr under vacuum. Solvents and starting materials distill first, followed by the desired product, which distills at 140°–150° C. at 0.3–0.4 mm Hg. The yield is 58.15 g. GC and 1H-NMR analysis show the presence of DMAC as well as a small amount of resorcinol and a trace (<1%) of the bis-benzocyclobutenyl ether of resorcinol. There is also a small amount of 3-(3-hydroxyphenoxy)benzocyclobutene, reflecting the small amount of 3-bromobenzocyclobutene in the 4-bromobenzocyclobutene. The purity is estimated at 87%; the yield of 4-(3-hydroxyphenoxy)-benzocyclobutene is thus 50.6 g (60%).

The product can be further purified by redistillation, if desired.

B. Preparation of Compound 5

To a 50 mL four neck round bottom flask is added 4-(N-methylamino)benzocyclobutene (1.33 g, 10.00 mmol), epichlorohydrin (0.46 g, 5.0 mmol), ethanol (15 mL), and sodium hydroxide (0.20 g, 5.00 mmol) in water (5 mL). The flask is fitted with a magnetic stir bar, a water-cooled condenser, and thermometer. The reaction mixture is stirred at 25° C. under nitrogen for 3 hours, then more NaOH (0.03 g, 0.75 mmol) in water (1 mL) is added. The solution is heated at 80° C. for 4 hours, which gives a homogeneous solution. When cooled to 25° C. a white precipitate forms, which is collected by filtration, and dried in vacuo at 25° C. for 16 hours. Yield: 0.77 g (48%). Compound 5 is identified by 1H and 13C NMR spectroscopy and cured according to the method described in Example 1, Part C. The glass transition temperatures of the cured resin is given in Table 1.

C. Additional Compounds

For the purposes of further exemplification, Compounds 1 and 6 are prepared by using the procedure described in Example 2, Part B using 4-hydroxybenzocyclobutene (1.20 g, 10.0 mmol) and 4-(3-hydroxyphenoxy)benzocyclobutene (2.12 g, 10.0 mmol) respectively in place of 4-(N-methylamino)benzocyclobutene. Both compounds are isolated by evaporating the reaction mixtures to dryness under reduced pressure followed by the addition of methylene chloride to dissolve the organic species. The mixtures are washed with water, the aqueous and organic layers are separated, and the organic layers are dried over magnesium sulfate to yield both compounds as thick oils. The oils are dried in vacuo at 80° C. to yield 1 and 6 respectively, which are identified by 1H and 13C NMR spectroscopy. The compounds are cured according to the method described in Example 1, Part C and the glass transition temperatures of the cured resins are given in Table 1.

Example 3

A. Preparation of Compound 7

To a 500 mL three-neck round-bottom flask fitted with a thermometer, a Teflon TM coated magnetic stir bar, and a nitrogen inlet is added bisphenol-A diglycidyl ether [139.44 g of epoxide equivalent weight (EEW) 174.3 g/equivalent weight epoxide, 0.80 equiv wt (or mol) epoxide], 4-hydroxybenzocyclobutene (96.12 g, 0.80 mol), and EtPh3PI (2.0 g, 4.8 mmol, 0.8 weight percent). The mixture is heated under nitrogen and gives a homogeneous melt at 100° C. Between 100° and 120° C., an exotherm develops which causes the melt to reach a temperature of 180° C. The melt is cooled to 120° C. with use of a water bath and is maintained at 120° C. for 24 hours. The slightly viscous melt is poured into a jar to yield 227 g (96%) of a light yellow, non-crystalline, glassy solid. The compound has a melt viscosity of 500 centipoise (cps) at 105° C. 1H and 13C NMR confirms the structure of Compound 7 shown below. The compound is cured according to the method described in Example 1, Part C and the glass transition temperature of the cured resin is given in Table 1.

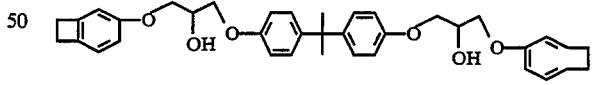

B. Bulk Monomer Curing

Compound 7 is cured by the procedure described in Example 1, Part D. Properties of the cured resin are measured and are reported in Table 2.

C. Additional Compounds

For the purposes of further exemplification, Compounds 8–11 are prepared by reacting bisphenol-A diglycidyl ether [1.70 g, 5.00 mmol, 10.0 mequiv wt (or mmol) epoxide] with 4-(3-hydroxyphenoxy)benzocyclobutene (2.12 g, 10.0 mmol), 4-mercaptobenzocyclobutene (1.36 g, 10.0 mmol), 4-(N-methylamino)benzocyclobutene (1.33 g, 10.0 mmol), and benzocyclobutene-4-carboxylic acid (1.48 g, 10.0 mmol), respectively, in place of 4-hydroxybenzocyclobutene, using the reaction procedure described in Example 1, Part E. EtPh3PI (0.02 g) is used during the preparation of compounds 8, 9, and 11, but is not required during the preparation of compound 10. Compounds 8-11 are identified by $^1$H and $^{13}$C NMR spectroscopy and are cured according to the method described in Example 1, Part C. Glass transition temperatures of the cured resins are given in Table 1.

EXAMPLE 4

A. Preparation of Compound 12

To a 250 mL one-neck round-bottom flask fitted with a thermometer, a Teflon TM coated magnetic stir bar, and a nitrogen inlet is added 9,9-bis(4-glycidyloxyphenyl)fluorene [51.20 g of EEW=239.0 g/equiv wt epoxide, 0.214 equiv wt (or mol) epoxide], 4-hydroxybenzocyclobutene (25.74 g, 0.214 mol), and EtPh3PI (0.4 g, 0.96 mmol, 0.5 weight percent). The mixture is heated under nitrogen to 130° C., during which time a homogeneous melt is obtained. An exotherm develops which causes the melt to reach a temperature of 150° C. The melt is allowed to cool to 130° C. and maintained at 130° C. for 24 hours. The viscous melt is poured into a jar to yield 71.4 g (93%) of a light yellow, non-crystalline, glassy solid. The compound has a melt viscosity of 500 centipoise (cps) at 145° C. $^1$H and $^{13}$C NMR confirms the structure of Compound 12 shown below. The compound is cured according to the method described in Example 1, Part C and the glass transition temperature of the cured resin is given in Table 1.

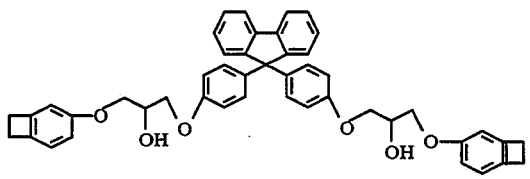

B. Bulk Monomer Curing

Compound 12 is cured by the procedure described in Example 1, Part D. Properties of the cured resin are measured and are reported in Table 2.

C. Additional Compounds

For the purposes of further exemplification, Compounds 13 and 14 are prepared by reacting 9,9-bis(4-glycidyloxyphenyl)fluorene [2.39 g of epoxy equiv wt (EEW) 239.0 g/equiv wt epoxide, 10.0 mequiv wt (or mmol) epoxide] with 4-(N-methylamino)benzocyclobutene (1.33 g, 10.0 mmol) and benzocyclobutene-4-carboxylic acid (1.48 g, 10.0 mmol), respectively, in place of 4-hydroxybenzocyclobutene, using the reaction procedure described in Example 1, Part E. EtPh3PI (0.02 g) is used during the preparation of Compound 14, but is not required during the preparation of Compound 13. Compounds 13 and 14 are identified by $^1$H and $^{13}$C M spectroscopy and are cured according to the method described in Example 1, Part C. Glass transition temperatures of the cured resins are given in Table 1.

EXAMPLE 5

Preparation of Compounds 15 and 22

Compounds 15 and 22 are prepared by reacting 4-hydroxybenzocyclobutene (2.40 g, 20.0 mmol) with hydroquinone diglycidyl ether [2.28 g of EEW=113.7 g/equiv wt epoxide, 20.0 mequiv wt (or mmol) epoxide] and the diglycidyl ether of N,N'-bis(3-hydroxyphenyl)-glutaramide [4.59 g of EEW=229.7 g/equiv wt epoxide, 20.0 mequiv wt (or mmol) epoxide] respectively in the presence of EtPh3PI (0.03 g) at 120° C. for 3 hours, using the reaction procedure described in Example 1, Part E. Compounds 15 and 22 are identified by $^1$H and $^{13}$C NMR spectroscopy and are cured according to the method described in Example 1, Part C. Glass transition temperatures of the cured resins are given in Table 1.

EXAMPLE 6

A. Preparation of Compound 16

To a 20 mL flask fitted with a magnetic stir bar, thermocouple, and nitrogen inlet is added 4-glycidyloxybenzocyclobutene (1.76 g, 10.0 mmol), 4,4'-sulfonyldiphenol (1.25 g, 5.00 mmol), and EtPh3PI (0.02 g). The contents of the flask are heated at 150° C. for 5 hours, during which time a viscous melt forms. Compound 16 is identified by 1H and 13C NMR spectroscopy and is cured according to the method described in Example 1, Part C. The glass transition temperature of the cured resin is given in Table 1.

B. Additional Compounds

For the purposes of further exemplification, Compounds 17-21, 23, 26-28, 30, and 32 are prepared by the procedure described in Example 6, Part A by reacting 4-glycidyloxybenzocyclobutene (1.76 g, 10.00 mmol) with the appropriate dihydridic compounds (H—A—H) from Table 1 (5.00 mmol), respectively, in place of 4,4'-sulfonyldiphenol. The preparation of Compounds 20 and 21 does not require the use of EtPh3PI catalyst. The compounds are identified by $^1$H and $^{13}$C NMR spectroscopy and are cured according to the method described in Example 1, Part C. Glass transition temperatures of the cured resins are given in Table 1.

EXAMPLE 7

A. Preparation of Compound 24

To a 20 mL flask fitted with a magnetic stir bar, thermocouple, and nitrogen inlet is added 4-glycidyloxybenzocyclobutene (1.76 g, 10.00 mmol), N-(4-hydroxyphenyl)-4-hydroxybenzamide (1.15 g, 5.00 mmol), EtPh3PI (0.02 g), and diethylene glycol dimethyl ether (1 mL). The contents of the flask are heated at 150° C. for 16 hours, during which time a solution forms. The solvent is removed from the mixture by heating in vacuo at 100° C. for 16 hours to yield 24 as a solid which melts near 170° C. as determined by DSC. Compound 24 is identified by $^1$H and $^{13}$C NMR spectroscopy and is cured according to the method described in Example 1, Part C. The glass transition temperature of the cured resin is given in Table 1.

B. Additional Compounds

For the purposes of further exemplification, Compounds 25, 29, and 31 are prepared by the procedure described in Example 7, Part A by reacting 4-glycidyloxybenzocyclobutene (1.76 g, 10.00 mmol) with the appropriate dihydridic compounds (H—A—H) from Table 1 (5.00 mol) respectively in place of N-(4-hydroxyphenyl)-4-hydroxybenzamide. The compounds are identified by $^1$H and $^{13}$C NMR spectroscopy and are cured according to the method described in Example 1, Part C. Glass transition temperatures of the cured resins are given in Table 1.

EXAMPLE 8

Preparation of Compound 33

To a 50 mL four neck round bottom flask is added 4-hydroxybenzocyclobutene (2.40 g, 20.0 mmol), bisphenol-A (2.28 g, 10.0 mmol), epichlorohydrin (1.85 g, 20.0 mmol), methoxyisopropanol (20 mL), and sodium hydroxide (0.80 g, 20.0 mmol) in water (5 mL). The flask is fitted with a magnetic stir bar, a water-cooled condenser, and thermometer. The reaction mixture is stirred at 25° C. under nitrogen for 16 hours, then more NaOH (0.12 g, 3.0 mmol) in water (5 mL) is added. The solution is heated at 90° C. for 6 hours, then cooled to 25° C. The reaction mixture is poured into diethyl ether (100 mL) and the aqueous and organic layers separate. The organic layer is collected and the aqueous layer is further extracted with methylene chloride (50 mL). The ether and methylene chloride extracts are combined and dried over magnesium sulfate, filtered, and the solvent allowed to evaporate. The residue is dried at 60° C. in vacuo for 16 hours to yield a non-crystalline glassy mass. Yield is 5.7 g (97%). The oligomeric product mixture is identified as Compound 33 (shown below) by reverse-phase liquid chromatography as well as by $^1$H and $^{13}$C NMR spectroscopy. Compound 33 is cured according to the method described in Example 1, Part C. Glass transition temperature of the cured resin is given in Table 1.

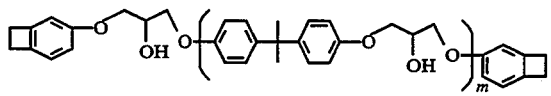

EXAMPLE 9

A. Preparation of Compound 34

To a 50 mL flask is added 4-hydroxybenzocyclobutene (2.40 g, 20.0 mmol), D.E.R. TM 661 epoxy resin [10.58 g of EEW=529.0 g/equiv epoxide, 20.0 mequiv wt (or mmol) epoxide], diethylene glycol dimethyl ether (5 mL), and EtPh$_3$PI (0.04 g). The flask is fitted with a magnetic stir bar, thermocouple, and nitrogen inlet. The contents of the flask are heated at 150° C. for 20 hours, then the solution is poured into a Teflon ® dish, and the solvent is removed slowly by heating the sample in vacuo between 25° and 100° C. over a 24 hour period. When cooled to 25° C., a light yellow, brittle solid remains which is identified as Compound 34 by reverse-phase liquid chromatography as well as $^1$H and $^{13}$C NMR spectroscopy. The product has a melt viscosity of 1300 centipoise at 150° C. Compound 34 is cured according to the method described in Example 1, Part C. Glass transition temperature of the cured resin is given in Table 1.

B. Additional Compounds

For the purposes of further exemplification, Compound 35 is prepared by using the procedure described in Example 9, Part A, using D.E.R. TM 669 epoxy resin (20.63 g of EEW=2063 g/equiv wt epoxide, 10.0 equiv wt epoxide), 4-hydroxybenzocyclobutene (1.20 g, 10.0 mmol), diethylene glycol dimethyl ether (30 mL), and EtPh$_3$PI (0.02 g). The product is identified by $^1$H and $^{13}$C NMR spectroscopy and is cured according to the method described in Example 1, Part C. The glass transition temperature of the cured resin is given in Table 1.

EXAMPLE 10

Preparation of Compound 36

Compound 7 from Example 3, Part A (0.58 g, 1.0 5 mmol) is dissolved in pyridine (20 mL) and to this solution is added acetic anhydride (20 mL) over a 30 minute period with stirring. On completion of addition, the solution is stirred at 25° C. for one hour then at 60° C. for an additional hour. When cool, the solution is poured into a mixture of 5% HCl and ice. The resulting viscous mass is dissolved in methylene chloride, washed with water, then dried over magnesium sulfate. The mixture is filtered to remove magnesium sulfate and the methylene chloride is allowed to evaporate. The product is dried at 80° C. in vacuo for 16 hours to yield a brown viscous mass. The product is identified as Compound 36 (below) by $^1$H and $^{13}$C NMR spectroscopy. Compound 36 is cured according to the method described in Example 1, Part C and has a glass transition temperature (Tg) of 107° C. as detected by DSC for the cured resin.

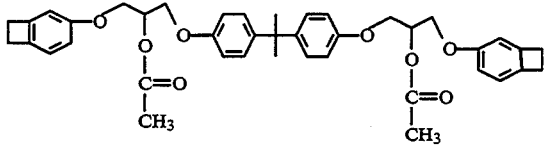

TABLE 1

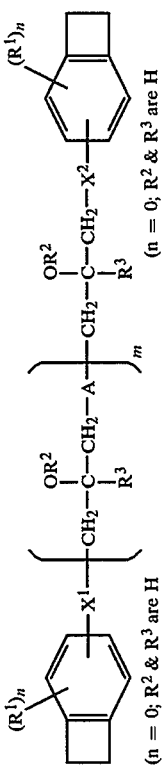

(n = 0; $R^2$ & $R^3$ are H)

| Compound | m | $X^1$ | A | $X^2$ | m.p.[a] (°C) | Cured $T_g$[b] (°C) |
|---|---|---|---|---|---|---|
| 1 | 0 | —O— | | —O— | 80 | 215 |
| 2 | 0 | —O— | | —S— | none[c] | 147 |
| 3 | 0 | —O— | | —CO$_2$— | none[c] | n.d.[d] |
| 4 | 0 | —O— | | —N(CH$_3$)— | none[c] | 175 |
| 5 | 0 | —N(CH$_3$)— | | —N(CH$_3$)— | none[c] | 148 |
| 6 | 0 | —O—C$_6$H$_4$—O— | | —O—C$_6$H$_4$—O— | none[c] | 139 |
| 7 | 1 | —O—C$_6$H$_4$—O— | —C$_6$H$_4$—C(CH$_3$)$_2$—C$_6$H$_4$— | —O—C$_6$H$_4$—O— | none[c] | 127 |
| 8 | 1 | —O—C$_6$H$_4$—O— | —C$_6$H$_4$—C(CH$_3$)$_2$—C$_6$H$_4$— | —S—C$_6$H$_4$—O— | none[c] | 86 |
| 9 | 1 | —S—C$_6$H$_4$—O— | —C$_6$H$_4$—C(CH$_3$)$_2$—C$_6$H$_4$— | —S—C$_6$H$_4$—O— | none[c] | 123 |
| 10 | 1 | —N(CH$_3$)— | —C$_6$H$_4$—C(CH$_3$)$_2$—C$_6$H$_4$— | —N(CH$_3$)— | none[c] | 118 |
| 11 | 1 | —CO$_2$— | —C$_6$H$_4$—C(CH$_3$)$_2$—C$_6$H$_4$— | —O$_2$C— | none[c] | 169 |

TABLE 1-continued
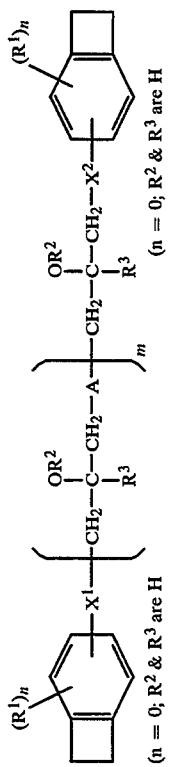
| Compound | m | $X^1$ | A | $X^2$ | m.p.[a] (°C.) | Cured $T_g$[b] (°C.) |
|---|---|---|---|---|---|---|
| 12 | 1 | —O— | 9,9-bis(4-hydroxyphenyl)fluorene derivative | —O— | none[c] | 193 |
| 13 | 1 | —N(CH₃)— | 9,9-bis(4-hydroxyphenyl)fluorene derivative | —N(CH₃)— | none[c] | 163 |
| 14 | 1 | —CO₂— | 9,9-bis(4-hydroxyphenyl)fluorene derivative | —O₂C— | none[c] | 220 |
| 15 | 1 | —O— | 1,4-dihydroxycyclohexadiene derivative | —O— | 129 | 142 |

TABLE 1-continued

Structure: [benzocyclobutene-(R¹)n]—X¹—CH₂—C(OR²)(R³)—CH₂—[A]ₘ—CH₂—C(OR²)(R³)—CH₂—X²—[benzocyclobutene-(R¹)n]
(n = 0; R² & R³ are H)

| Compound | m | X¹ | A | X² | m.p.[a] (°C) | Cured Tg[b] (°C) |
|---|---|---|---|---|---|---|
| 16 | 1 | —O— | 4-methoxyphenyl–SO₂–4-phenyl | —O— | none[c] | 173 |
| 17 | 1 | —O— | diphenyl(phenyl)methane (bis(4-hydroxyphenyl)phenylmethane) | —O— | none[c] | 149 |
| 18 | 1 | —O— | bis(3,5-dibromo-4-hydroxyphenyl)methane | —O— | none[c] | n.d.[d] |
| 19 | 1 | —O— | 9,9-bis(4-methoxyphenyl)-2,7-dinitrofluorene | —O— | none[c] | n.d.[d] |
| 20 | 1 | —O— | piperazine (N—N) | —O— | 155 | 147 |

TABLE 1-continued

| Compound | m | $X^1$ | A | $X^2$ | m.p.[a] (°C) | Cured $T_g$[b] (°C) |
|---|---|---|---|---|---|---|
| 21 | 1 | —O— | —N(—CH₂CH₂OH)— | —O— | none[c] | 107 |
| 22 | 1 | —O— | 4-MeO-C₆H₄-NH-C(=O)-(CH₂)₃-C(=O)-NH-C₆H₄-4-OMe | —O— | none[c] | 139 |
| 23 | 1 | —O— | 4-MeO-C₆H₄-NH-C(=O)-CH₂-CH₂-C(=O)-C₆H₄-4-OMe | —O— | 145–165 | 165 |
| 24 | 1 | —O— | 4-MeC₆H₄-N(H)-C(=O)-C₆H₄-4-OMe | —O— | 170 | 182 |
| 25 | 1 | —O— | bis-phthalimide linked by benzophenone (4,4'-carbonyl-bis(phthalimido-N-CH₂—O—)) | —O— | none[c] | 175 |
| 26 | 1 | —O— | 1,4-C₆H₄(SO₂N(CH₃)—)₂ | —O— | none[c] | 116 |

Structural header:

(R¹)ₙ-benzocyclobutene—X¹—CH₂—C(OR²)(R³)—[CH₂—A—]ₘ—CH₂—C(OR²)(R³)—CH₂—X²—benzocyclobutene-(R¹)ₙ

(n = 0; R² and R³ are H)

TABLE 1-continued

| Compound | m | X¹ | A | X² | m.p.[a] (°C) | Cured $T_g$[b] (°C) |
|---|---|---|---|---|---|---|
| 27 | 1 | —O— | 1,4-phenylene dicarboxylate | —O— | none[c] | 138 |
| 28 | 1 | —O— | 1,3-phenylene dicarboxylate | —O— | 115 | 149 |
| 29 | 1 | —O— | 2,6-naphthalene dicarboxylate | —O— | none[c] | 165 |
| 30 | 1 | —O— | 4,4'-biphenyl dicarboxylate | —O— | none[c] | 174 |
| 31 | 1 | —O— | 2,6-naphthalene dicarboxylate | —O— | 150 | n.d.[d] |
| 32 | 1 | —O— | 1,4-phenylene (ether-carboxylate) | —O— | none[c] | 149 |

TABLE 1-continued

[Structure shown at top of table:]

(R¹)ₙ — X¹ — [ CH₂—C(OR²)(R³)—CH₂—A ]ₘ — CH₂—C(OR²)(R³)—CH₂—X² — (R¹)ₙ

(n = 0; R² & R³ are H)     (n = 0; R² & R³ are H)

| Compound | m | X¹ | A | X² | m.p.$^a$ (°C.) | Cured Tg$^b$ (°C.) |
|---|---|---|---|---|---|---|
| 33 | 0–7$^e$ | —O— | —O—C₆H₄—C(CH₃)₂—C₆H₄—O— | —O— | none$^c$ | 134 |
| 34 | 3.5$^f$ | —O— | —O—C₆H₄—C(CH₃)₂—C₆H₄—O— | —O— | none$^c$ | 111 |
| 35 | 15$^f$ | —O— | —O—C₆H₄—C(CH₃)₂—C₆H₄—O— | —O— | none$^c$ | 94 |

$^a$Approximate melting point of the as synthesized material as determined by the differential scanning calorimetry.
$^b$Glass transition temperature (Tg) of the resin after curing by DSC analysis (50–300° C., rate of 10° C./minute).
$^c$'None' refers to the absence of a melting endotherm as determined by DCS.
$^d$Tg not detected (n.d.) by DSC after curing.
$^e$Average m = 1.0 but contains compounds of m = 0–7.
$^f$Exists as a series of oligomers with an average m as shown in the table.

TABLE 2

| | Cured Resin Properties | | |
|---|---|---|---|
| Cured Compound | 1 | 7 | 12 |
| Density (g/cm$^3$) | 1.22 | 1.20 | 1.22 |
| Tg by DMA (°C.) | 236 | 122 | 192 |
| Temp. at 1% wt loss in N$_2$ (°C.) | 350 | 334 | 350 |
| Flex Strength (ksi) | 16.6 | 19.7 | 17.2 |
| Flex Modulus (Ksi) | 478 | 505 | 482 |
| K$_{1C}$ (psi-in$^{\frac{1}{2}}$) | 502 | 655 | 454 |
| CTE (ppm/°C.) (50–100° C.) | 53 | 68 | 67 |

What is claimed is:

1. A compound of the formula:

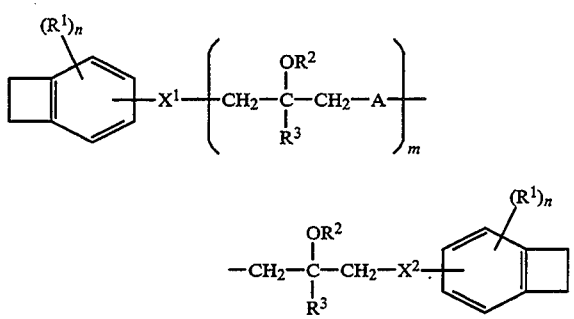

wherein R$^1$ is halogen, monovalent hydrocarbyl, or substituted hydrocarbyl; each R$^2$ is independently hydrogen, monovalent hydrocarbyl or substituted hydrocarbyl or acyl; each R$^3$ is independently hydrogen, monovalent hydrocarbyl or substituted hydrocarbyl, wherein the substituent(s) is a monovalent moiety which is inert in the reactions used in preparing the compound; each of X$^1$ and X$^2$ is independently oxygen, sulfur, N-substituted imino, N-substituted sulfonamido, carboxyl, or dioxyarylene; each A is individually a divalent organic moiety; n=0–3; and m=0–1000.

2. The compound of claim 1 wherein R$^1$ is halogen, alkyl, or aryl; R$^2$ is individually hydrogen, alkyl, cycloalkyl, aralkyl, aryl, or acyl; R$^3$ is individually hydrogen, alkyl, cycloalkyl, aralkyl, or aryl; n=0 or 1; and m=0.

3. The compound of claim 2 wherein n=0; each of X$^1$ and X$^2$ is independently oxygen, sulfur, N-methylimino, N-methylsulfonamido, carboxyl, or dioxyarylene; R$^2$ is hydrogen or acyl; and R$^3$ is hydrogen.

4. The compound of claim 3 wherein X$^1$ is oxygen; X$^2$ is independently oxygen, sulfur, N-methylimino, or carboxyl; and R$^2$ is hydrogen.

5. The compound of claim 3 wherein each of X$^1$ and X$^2$ is 1,3-dioxyphenylene; and R$^2$ is hydrogen.

6. The compound of claim 3 wherein each of X$^1$ and X$^2$ is N-methylimino; and R$^2$ is hydrogen.

7. The compound of claim 3 formed by contacting a benzocyclobutene species containing an epoxy moiety on the arylene ring with a benzocyclobutene species containing a functionality on the arylene ring capable of reacting with an epoxy group.

8. The compound of claim 3 formed by contacting an epihalohydrin with a benzocyclobutene species containing a functionality on the arylene ring capable of reacting with an epoxy group.

9. The compound of claim 1 wherein R$^1$ is halogen, alkyl, or aryl; R$^2$ is individually hydrogen, alkyl, cycloalkyl, aralkyl, aryl, or acyl; R$^3$ is individually hydrogen, alkyl, cycloalkyl, aralkyl, or aryl; each of X$^1$ and X$^2$ is independently oxygen, sulfur, N-substituted imino, N-substituted sulfonamido, carboxyl, or dioxyarylene; each A is individually a divalent moiety represented by the formula:

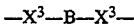

wherein B is individually a divalent organic moiety; X$^3$ is independently oxygen, sulfur, N-substituted imino, N-substituted sulfonamido, carboxyl, or dioxyarylene; n=0 or 1; and m=1–50.

10. The compound of claim 9 wherein n=0; m=1; R$^2$ is hydrogen or acetyl; R$^3$ is hydrogen; X$^1$ is oxygen, sulfur, N-methylimino, N-methylsulfonamido, carboxyl, or dioxyarylene; X$^2$ is independently oxygen, sulfur, N-methylimino, N-methylsulfonamido, carboxyl, or dioxyarylene; X$^3$ is independently oxygen, sulfur, N-methylimino, N-methylsulfonamido, carboxyl, or dioxyarylene; and B is a divalent aromatic moiety.

11. The compound of claim 10 wherein R$^2$ is hydrogen; each of X$^1$ and X$^2$ is oxygen; X$^3$ is independently oxygen, N-methylsulfonamido, or carboxyl; and B is isopropylidenediphenylene, fluorenylidenediphenylene, dinitrofluorenylidenediphenylene, phenylene, sulfonyldiphenylene, biphenylene, oxydiphenylene, thiodiphenylene, methylenediphenylene, phenylethylidenediphenylene, tetrabromoisopropylidenediphenylene, naphthylene, bis[(N-phenyleneamido)propylidene, bis(benzamido)ethylene, amidodiphenylene, or [bis(N-methylenephthalimido)]carbonyl.

12. The compound of claim 10, wherein each of X$^1$ and X$^2$ is N-methylimino; X$^3$ is oxygen; B is isopropylidenediphenylene or fluorenylidenediphenylene; and R$^2$ is hydrogen.

13. The compound of claim 10, wherein each of X$^1$ and X$^2$ is carboxyl; X$^3$ is oxygen; B is isopropylidenediphenylene or fluorenylidenediphenylene; and R$^2$ is hydrogen.

14. The compound of claim 9 formed by contacting a diepoxide species with a benzocyclobutene species containing a functionality on the arylene ring capable of reacting with an epoxy group.

15. The compound of claim 9 formed by contacting a benzocyclobutene species containing an epoxy moiety on the arylene ring with a species containing two functionalities capable of reacting with an epoxy group.

16. The compound of claim 1 wherein R$^1$ is halogen, alkyl, or aryl; R$^2$ is individually hydrogen, alkyl, cycloalkyl, aralkyl, aryl, or acyl; R$^3$ is individually hydrogen, alkyl, cycloalkyl, aralkyl, or aryl; X$^1$ is oxygen, sulfur, N-substituted imino, N-substituted sulfonamido, carboxyl, or dioxyarylene; X$^2$ is independently oxygen, sulfur, N-substituted imino, N-substituted sulfonamido, carboxyl, or dioxyarylene; each A is individually a divalent moiety represented by the formulae:

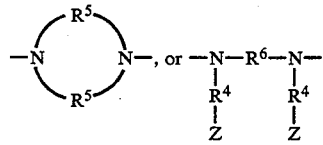

wherein $R^4$ is $C_2$–$C_{10}$ alkylene or arylene, substituted $C_2$–$C_{10}$ alkylene or arylene, wherein the substituent is alkylamido, hydroxyl, alkoxy, acyl, aryloxy, halo, or cyano; $R^5$ is $C_2$–$C_{10}$ alkylene or substituted $C_2$–$C_{10}$ alkylene, wherein the substituent is alkylamido, hydroxyl, alkoxy, acyl, aryloxy, halo, or cyano; $R^6$ is arylene, a $C_2$–$C_{20}$ alkylene, or substituted $C_2$–$C_{20}$ alkylene wherein the substituent is alkylamido, hydroxyl, alkoxy, acyl, aryloxy, halo, or cyano; Z is hydrogen, alkylamido, hydroxyl, alkoxy, acyl, aryloxy, halo, or cyano; n=0 or 1; and m=1–50.

17. The compound of claim 16 wherein n=0; m=1; $R^2$ is hydrogen or acetyl; $R^3$ is hydrogen; $X^1$ is oxygen, sulfur, N-substituted imino, N-substituted sulfonamido, carboxyl, or dioxyarylene; $X^2$ is independently oxygen, sulfur, N-substituted imino, N-substituted sulfonamido, carboxyl, or dioxyarylene; $R^4$ is ethylene, propylene, butylene, phenylene, biphenylene, or naphthylene; each of $R^5$ and $R^6$ is ethylene or propylene; and Z is hydrogen, methyl, methoxy, or hydroxy.

18. The compound of claim 17, wherein $R^2$ is hydrogen; each of $R^4$, $R^5$, and $R^6$ is ethylene; Z is hydroxy; and each of $X^1$ and $X^2$ is oxygen.

19. The compound of claim 16 formed by contacting a species containing tertiary amino groups and two glycidyl groups with a benzocyclobutene species containing a functionality on the arylene ring capable of reacting with an epoxy group.

20. The compound of claim 16 formed by contacting a benzocyclobutene species containing an epoxy moiety on the arylene ring with an amino species containing two N-H functionalities capable of reacting with an epoxy group.

21. The compound of claim 9 wherein n=0; m=0–10; $R^2$ is hydrogen or acetyl; $R^3$ is hydrogen; $X^1$ is oxygen, sulfur, N-substituted imino, N-substituted sulfonamido, carboxyl, or dioxyarylene; $X^2$ is independently oxygen, sulfur, N-substituted imino, N-substituted sulfonamido, carboxyl, or dioxyarylene; $X^3$ is independently oxygen, sulfur, N-substituted imino, N-substituted sulfonamido, carboxyl, or dioxyarylene; and B is a divalent aromatic moiety.

22. The compound of claim 21 wherein $R^2$ is hydrogen; $X^1$ is oxygen or N-methylimino; $X^2$ is independently oxygen or N-methylimino; $X^3$ is independently oxygen or N-methylsulfonamido; B is isopropylidenediphenylene, fluorenylidenediphenylene, dinitrofluorenylidenediphenylene, phenylene, sulfonyldiphenylene, biphenylene, biphenylene oxide, biphenylene sulfide, methylenediphenylene, phenylethylidenediphenylene, tetrabromoisopropylidenediphenylene, naphthylene, bis[(N-phenyleneamido)propylidene, bis(benzamido)ethylene, or amidodiphenylene.

23. The compound of claim 22 wherein each of $X^1$, $X^2$, and $X^3$ is oxygen, and B is isopropylidenediphenylene.

24. The compound of claim 21 formed by contacting an epihalohydrin with (1) a species or mixture of species each containing two functionalities capable of reacting with an epoxy group and (2) a benzocyclobutene species containing a functionality on the arylene ring capable of reacting with an epoxy group.

25. The compound of claim 9 wherein n=0; m=1–25; each of $X^1$, $X^2$, and $X^3$ is oxygen, B is isopropylidenediphenylene, and each of $R^2$ and $R^3$ is hydrogen.

26. The compound of claim 25 formed by contacting a diepoxide species with a benzocyclobutene species containing a functionality capable of reacting with an epoxy group.

27. A thermoset polymer prepared from the compound of claim 1.

28. The polymer of claim 27 as a matrix resin for composites.

29. The polymer of claim 27 as an adhesive.

30. The polymer of claim 27 as a coating.

31. The polymer of claim 27 as a binder.

32. The polymer of claim 27 as a molded article.

33. The polymer of claim 27 as a film.

* * * * *